US011298397B2

(12) United States Patent
Nagano et al.

(10) Patent No.: US 11,298,397 B2
(45) Date of Patent: Apr. 12, 2022

(54) HEMOSTATIC COMPOSITION AND HEMOSTATIC METHOD USING HEMOSTATIC COMPOSITION

(71) Applicant: 3-D MATRIX, LTD., Tokyo (JP)

(72) Inventors: Keiji Nagano, Tokyo (JP); Satoru Kobayashi, Tokyo (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 16/060,269

(22) PCT Filed: Dec. 14, 2016

(86) PCT No.: PCT/JP2016/087298
§ 371 (c)(1),
(2) Date: Jun. 7, 2018

(87) PCT Pub. No.: WO2017/104723
PCT Pub. Date: Jun. 22, 2017

(65) Prior Publication Data
US 2018/0360904 A1    Dec. 20, 2018

(30) Foreign Application Priority Data
Dec. 18, 2015 (JP) .............................. JP2015-247334

(51) Int. Cl.
| | |
|---|---|
| *A61K 38/04* | (2006.01) |
| *A61K 9/12* | (2006.01) |
| *A61K 38/00* | (2006.01) |
| *C07K 7/00* | (2006.01) |
| *A61L 26/00* | (2006.01) |
| *A61K 38/10* | (2006.01) |
| *A61K 9/70* | (2006.01) |
| *A61K 38/08* | (2019.01) |
| *A61P 7/04* | (2006.01) |
| *A61P 17/02* | (2006.01) |

(52) U.S. Cl.
CPC ............... *A61K 38/04* (2013.01); *A61K 9/12* (2013.01); *A61K 9/7015* (2013.01); *A61K 38/00* (2013.01); *A61K 38/08* (2013.01); *A61K 38/10* (2013.01); *A61L 26/0028* (2013.01); *A61L 26/0076* (2013.01); *A61P 7/04* (2018.01); *A61P 17/02* (2018.01); *C07K 7/00* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 9,415,084 B2 | 8/2016 | Ellis-Behnke et al. | |
| 10,369,237 B2 | 8/2019 | Gil et al. | |
| 10,576,123 B2 * | 3/2020 | Takamura | A61K 31/7004 |
| 2006/0084607 A1 | 4/2006 | Spirio et al. | |
| 2007/0203062 A1 | 8/2007 | Ellis-Behnke et al. | |
| 2011/0201541 A1 | 8/2011 | Takamura et al. | |
| 2016/0317607 A1 | 11/2016 | Spirio et al. | |
| 2016/0317807 A1 | 11/2016 | Spirio et al. | |

FOREIGN PATENT DOCUMENTS

| | | | |
|---|---|---|---|
| JP | 2008505919 | | 2/2008 |
| JP | 2008/539257 | | 11/2008 |
| JP | 2010-521495 | | 6/2010 |
| WO | 2006/116524 | | 11/2006 |
| WO | 2010/041636 | | 4/2010 |
| WO | WO 2010/041636 | * | 4/2010 |
| WO | 2015/098515 | | 7/2015 |

OTHER PUBLICATIONS

Lee et al. ("A novel hemostatic agent based on self-assembling peptides in the setting of nasal endoscopic surgery, a case series" Int J Surg Case Rep. 2017; 461-464).*
Yoshida et al. ("Initial clinical trial of a novel hemostat, TDM-621, in the endoscopic treatment of gastric tumors" Journal of Gastroenterology and Hepatology, Dec. 18, 2014).*
Simply Psychology (https://www.simplypsychology.org/p-value.html).*
Komatsu, Seiji "The Neutral Self-Assembling Peptide Hydrogel SPG-178 as a Topical Hemostatic Agent", PLoS One, 9(7):1-8 (2014).
English Translation of Written Opinion and International Search Report corresponding to International Application No. PCT/JP2016/087298, dated Feb. 28, 2017, 9 pages.
Ellis-Behnke et al. "Nano hemostat solution: immediate hemostasis at the nanoscale" Nanomedicine: Nanotechnology, Biology, and Medicine 2, 207-215 2006.

* cited by examiner

*Primary Examiner* — James H Alstrum-Acevedo
*Assistant Examiner* — Tara L Martinez
(74) *Attorney, Agent, or Firm* — Myers Bigel, P.A.

(57) ABSTRACT

[Problem] To provide a composition for hemostasis that can be applied uniformly to a bleeding site and exerts a high hemostatic effect. [Solution] Provided is a composition to be applied to the subject as a spray, wherein the composition is characterized in that the spray is for hemostasis, and the composition includes a self-assembling peptide, the self-assembling peptide gelling due to self-assembly when the composition is applied to the bleeding site of the subject, and the self-assembling peptide being included in the composition in a concentration having an improved hemostatic capacity in comparison to direct application.

3 Claims, 6 Drawing Sheets

Specification includes a Sequence Listing.

Usual application

Usual application

Spray application

Peptide No.1 1.0%

Spray application

Peptide No.1 1.5%

Usual application

Usual application

Spray application

Spray application

Peptide No.1 2.0%                    Peptide No.1 2.5%

Usual application

Usual application

Spray application

Peptide No.2 1.0%

Spray application

Peptide No.2 1.5%

Usual application

Spray application

Peptide No.3 1.5%

| Test substance | Application method | Hemostasis completion time (sec) | Applied amount (ml/cm²) |
|---|---|---|---|
| Peptide No.1 1.0% | Usual | 123 | 0.4 |
| | Usual | Failure of hemostasis | 0.73 |
| | Spray | 90 | 0.28 |
| | Spray | Failure of hemostasis | 0.71 |
| Peptide No.1 1.5% | Usual | Failure of hemostasis | 0.73 |
| | Spray | 137 | 0.54 |
| Peptide No.1 2.0% | Usual | 265 | 1.01 |
| | Spray | 170 | 0.32 |
| Peptide No.1 2.5% | Usual | 120 | 0.4 |
| | Spray | 45 | 0.2 |

```
SEQUENCE LISTING

<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: synthetic peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: synthetic peptide

<400> SEQUENCE: 2

Ile Glu Ile Lys Ile Glu Ile Lys Ile Glu Ile Lys Ile
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic peptide

<400> SEQUENCE: 3

Arg Leu Asp Leu Arg Leu Ala Leu Arg Leu Asp Leu Arg
1               5                   10
```

HEMOSTATIC COMPOSITION AND HEMOSTATIC METHOD USING HEMOSTATIC COMPOSITION

STATEMENT OF PRIORITY

This application is a 35 U.S.C. § 371 national phase application of International Application Serial No. PCT/JP2016/087298, filed Dec. 14, 2016, which claims the benefit, under 35 U.S.C. § 119 (a) of Japanese Patent Application No. 2015-247334, filed Dec. 18, 2015, the entire contents of each of which are incorporated by reference herein.

TECHNICAL FIELD

The present invention relates to a spray for hemostasis comprising a self-assembling peptide.

BACKGROUND ART

Biogels such as fibrin glue are utilized in perioperative or postoperative hemostats, surgical base materials such as wound healing sheets, drug delivery systems (DDSs), etc.

However, most of these biogels employ organism-derived materials and therefore have the risk of infection by microbes such as viruses, immunogenicity, propagation of diseases, etc. when used. For example, fibrin glue, albeit highly useful as a perioperative hemostat, has become a significant social problem due to frequent accidents causing the infection of patients by hepatitis virus contaminants in the fibrin glue when actually used in operation, because its raw material is derived from human blood. Accordingly, there is a demand for the development of a safe hemostat without the risk of microbial contamination by the chemical synthesis of its raw material.

For example, use of a composition comprising a purified amphipathic self-assembling peptide in the promotion of wound healing, etc. has been proposed so far (Patent Literature 1).

CITATION LIST

Patent Literature

Patent Literature 1: National Publication of International Patent Application No. 2008-505919

SUMMARY OF INVENTION

Technical Problem

The self-assembling peptide composition as described in Patent Literature 1 is a very useful composition because this composition can promote tissue regeneration by application to a wound site (or an operative site) and has no risk of microbial contamination.

The present inventors have tackled application research on the self-assembling peptide as described above and consequently found that in the case of using the self-assembling peptide as described above for hemostasis (e.g., for a hemostat for use in surgical operation), there is a technical dilemma, i.e., a higher concentration of the peptide in a composition to be applied to a bleeding site improves a hemostatic effect, but elevates the viscosity of the composition to be applied so that the applied composition is difficult to spread at the bleeding site and thus has the difficulty in exerting a uniform hemostatic effect at the application site (in other words, a lower concentration of the peptide in the composition to be applied to a bleeding site facilitates spreading the applied composition at the bleeding site, but does not produce a high hemostatic effect).

The present inventors have conducted diligent studies on a method for overcoming the technical dilemma described above and consequently completed the present invention by finding that, surprisingly, by using a composition comprising a self-assembling peptide as a "spray", the composition comprising a self-assembling peptide can be uniformly applied to a bleeding site and produces a high hemostatic effect as compared with that when applied by a conventional method.

Solution to Problem

Specifically, in one embodiment, the present invention relates to a composition to be applied as a spray to a subject, the spray being used for hemostasis, and the composition comprising a self-assembling peptide, wherein the self-assembling peptide self-assembles and thereby gels when the composition is applied to a bleeding site of the subject, and the self-assembling peptide is contained in the composition at a concentration at which the composition has an improved hemostatic ability as compared with that when directly applied.

In one embodiment of the present invention, the concentration of the self-assembling peptide in the composition is at least 1.5% by weight or higher.

In one embodiment of the present invention, the self-assembling peptide is (a) a peptide comprising an amino acid sequence consisting of 4 to 34 amino acid residues, wherein polar amino acid residues and nonpolar amino acid residues are alternately arranged, or (b) a peptide comprising an amino acid sequence consisting of 13 amino acid residues, wherein nonpolar amino acids and polar amino acids are arranged alternately and at symmetric positions in directions toward the N terminus and the C terminus centered on a nonpolar amino acid residue at position 7.

In one embodiment of the present invention, the polar amino acid residues are amino acid residues selected from the group consisting of an aspartic acid residue, a glutamic acid residue, an arginine residue, a lysine residue, a histidine residue, a tyrosine residue, a serine residue, a threonine residue, an asparagine residue, a glutamine residue, and a cysteine residue.

In one embodiment of the present invention, the nonpolar amino acid residues are amino acid residues selected from the group consisting of an alanine residue, a valine residue, a leucine residue, an isoleucine residue, a methionine residue, a phenylalanine residue, a tryptophan residue, a proline residue, and a glycine residue.

In one embodiment of the present invention, the polar amino acid residues are amino acid residues selected from the group consisting of an aspartic acid residue, a glutamic acid residue, an arginine residue, a lysine residue, a histidine residue, a tyrosine residue, a serine residue, a threonine residue, an asparagine residue, a glutamine residue, and a cysteine residue, and the nonpolar amino acid residues are amino acid residues selected from the group consisting of an alanine residue, a valine residue, a leucine residue, an isoleucine residue, a methionine residue, a phenylalanine residue, a tryptophan residue, a proline residue, and a glycine residue.

In one embodiment of the present invention, the self-assembling peptide is a peptide comprising RADARADARADARADA (SEQ ID NO: 1), a peptide comprising IEIKIEIKIEIKI (SEQ ID NO: 2), or a peptide comprising RLDLRLALRLDLR (SEQ ID NO: 3).

In one embodiment of the present invention, the self-assembling peptide is a peptide consisting of RADARADARADARADA (SEQ ID NO: 1), a peptide consisting of IEIKIEIKIEIKI (SEQ ID NO: 2), or a peptide consisting of RLDLRLALRLDLR (SEQ ID NO: 3).

In one embodiment of the present invention, the bleeding site of the subject is a non-surgically formed wound site or a surgically formed incision site or excision site.

In an alternative embodiment, the present invention relates to use of any of the compositions described above for the production of a spray for hemostasis.

In an alternative embodiment, the present invention relates to a spray comprising any of the compositions described above.

In an alternative embodiment, the present invention relates to a method for hemostasis in a subject, comprising the step of applying a composition comprising a self-assembling peptide to a bleeding site of the subject by spraying, wherein the self-assembling peptide self-assembles and thereby gels when the composition is applied to the bleeding site of the subject, and the self-assembling peptide is contained in the composition at a concentration at which the composition has an improved hemostatic ability as compared with that when directly applied.

In one embodiment of the present invention, the subject is a nonhuman animal.

Any combination of one or more of the features of the present invention described above is also included in the scope of the present invention.

DESCRIPTION OF EMBODIMENTS

Figure 1:
FIG. 1 shows a syringe packed with a peptide solution, used in Examples of the present invention.
Figure 2:
FIG. 2 shows photographs taken after application of Peptide No. 1 (1.0% or 1.5%) to a bleeding site of the porcine liver by usual application or spray application.
Figure 2:
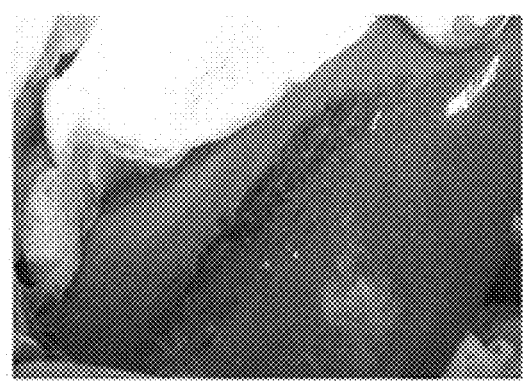
Figure 2:
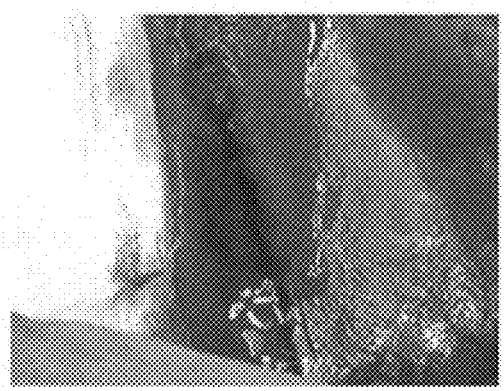
Figure 2:
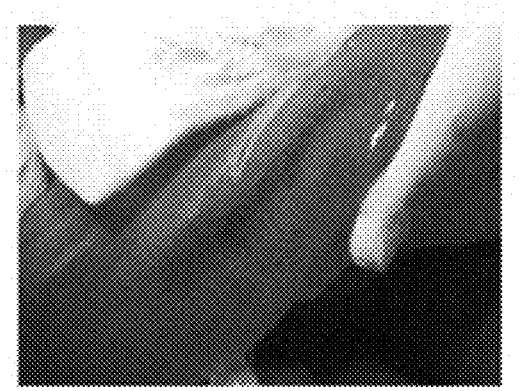
Figure 3:
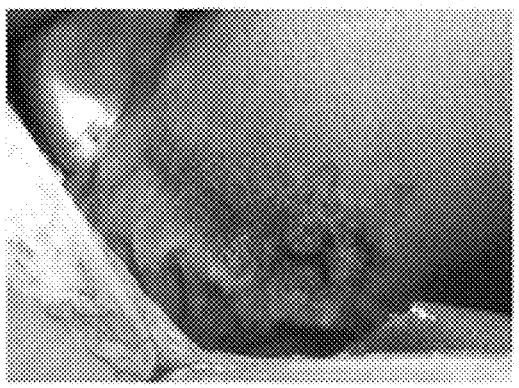
FIG. 3 shows photographs taken after application of Peptide No. 1 (2.0% or 2.5%) to a bleeding site of the porcine liver by usual application or spray application.
Figure 3:
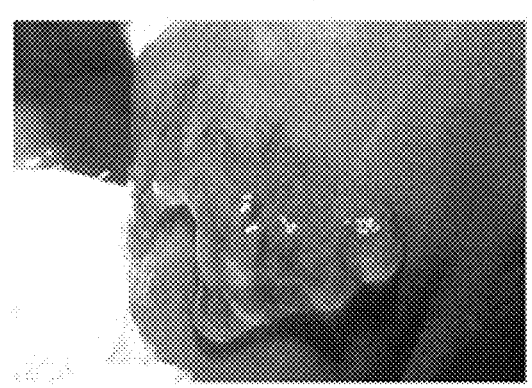
Figure 3:
Figure 3:
Figure 4:
FIG. 4 shows photographs taken after application of Peptide No. 2 (1.0% or 1.5%) to a bleeding site of the porcine liver by usual application or spray application.
Figure 4:
Figure 4:
Figure 4:
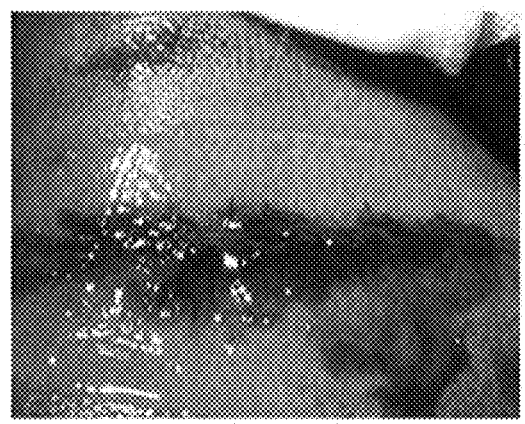
Figure 5:
FIG. 5 shows photographs taken after application of Peptide No. 3 (1.5%) to a bleeding site of the porcine liver by usual application or spray application.
Figure 5:
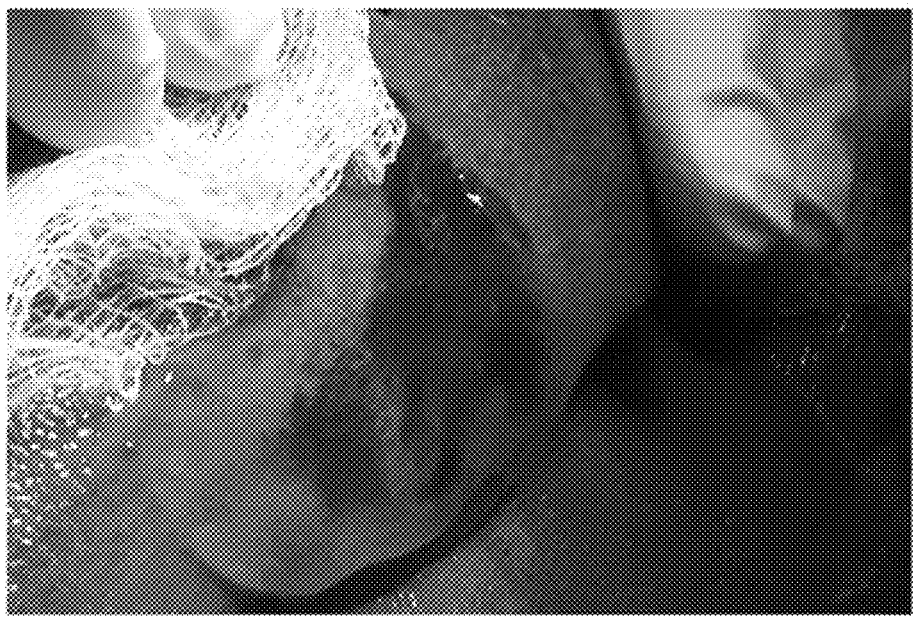

The present invention relates to a composition to be applied as a spray to a subject. In the present invention, the "spray" means an agent that is applied in a spray form to a recipient subject. In the present invention, a method, an instrument or an apparatus for applying the composition in a spray form is not limited and can be appropriately selected by those skilled in the art. The composition can be applied in a spray form, for example, by spraying a liquid composition in a state such as a mist or a foam using compressed air or high-pressure gas. More specifically, the composition can be applied in a spray form, for example, through the use of a can spray based on internal high-pressure gas, an electric spray based on an electric pump or the like, or an air spray (e.g., a spray gun or an air brush) based on external air pressure.

The present invention also relates to an agent for hemostasis. In the present invention, the agent "for hemostasis" broadly means an agent that is used for arresting bleeding from a living body and includes not only an agent that completely arrests bleeding but an agent that alleviates bleeding.

The bleeding site which is subject to the hemostasis according to the present invention may be any site. The present invention can be used in, for example, the hemostasis of a non-surgically formed wound site or a surgically formed incision site or excision site. Examples of the non-surgically formed wound site can include wound sites of body surface tissues (e.g., the skin) or body tissues (e.g., organs, muscles, and bones) caused by accidents, etc. Examples of the surgically formed incision site or excision site can include sites of body surface tissues or body tissues incised or excised with a surgical knife or the like in surgical procedures, and sites of body surface tissues or body tissues exfoliated, anastomosed, sutured, etc. with a surgical instrument. The present invention is applied to a subject by spraying and therefore permits easier application operation than that of conventional products in such a way that the composition is uniformly applicable to a wide range by single operation. Thus, the present invention can also be suitably used for a bleeding site resulting from, for example, endoscopic operation which requires careful operation.

The recipient subject of the present invention can be a human or nonhuman subject. The nonhuman subject can be, for example, a nonhuman animal and can be, for example, a nonhuman mammal, bird, a reptile, an amphibian, or fish. Examples of the nonhuman mammal include rodents (e.g., mice and rats), dogs, cats, horses, pigs, cattle, sheep, goat, and primates The composition of the present invention comprises a self-assembling peptide. In the present specification, the phrase "peptide "self-assembles" in a solution" means that the molecules of the peptide assemble spontaneously via any interaction (e.g., electrostatic interaction, a hydrogen bond, a van der Waals' force, or hydrophobic interaction) in the solution, and must not be interpreted in a limited meaning. In the present invention, the self-assembling peptide means a peptide having a property of forming a self-assembly form in which many peptide molecules are regularly arranged according to their amino acid sequences. Owing to this property, when the composition comprising the self-assembling peptide is applied to a bleeding site of the subject, the self-assembling peptide self-assembles and thereby forms a gel at the application site.

The self-assembling peptide used in the present invention may have given viscosity of its aqueous solution (i.e., an aqueous peptide solution before self-assembly of the self-assembling peptide) itself before application to the subject. However, in the present specification, such an aqueous peptide solution before application to the subject is also referred to as a "peptide solution (or aqueous peptide solution)" even when having given viscosity, for the sake of convenience of explanation. Also, even when the aqueous peptide solution before application to the subject has given viscosity, further elevation in the viscosity of the composition by the self-assembly of the self-assembling peptide after application of the aqueous solution to the subject is also referred to as "gelling (or gel formation)".

The self-assembling peptide used in the present invention can be, for example, a peptide comprising an amino acid sequence consisting of 4 to 34 amino acid residues, wherein polar amino acid residues and nonpolar amino acid residues are alternately arranged, or a peptide comprising an amino acid sequence consisting of 13 amino acid residues, wherein nonpolar amino acids and polar amino acids are arranged alternately and at symmetric positions in directions toward the N terminus and the C terminus centered on a nonpolar amino acid residue at position 7.

By having the peptide structure as described above, the self-assembling peptide used in the present invention forms a β sheet structure in an aqueous solution such that only the polar amino acid residues can be arranged on one surface of the β sheet structure while only the nonpolar amino acid residues can be arranged on the other surface. Thus, such β sheet structures are capable of forming a two-layer structure by assembling so as to conceal their hydrophobic surfaces (surfaces on which only the nonpolar amino acid residues are arranged). Furthermore, as the self-assembly of the molecules proceeds, this layer structure of the β sheets is capable of elongating to form a three-dimensional conformational structure (e.g., a hydrogel). The "self-assembling peptide" used in the present invention is also referred to as a "self-organizing peptide" in some cases.

The self-assembling peptide used in the present invention may comprise an "amino acid sequence in which polar amino acid residues and nonpolar amino acid residues are alternately arranged". In this case, the amino acid sequence can be an amino acid sequence consisting of 4 to 34 amino acid residues, more preferably an amino acid sequence consisting of 8 to 30 amino acid residues, further preferably an amino acid sequence consisting of 12 to 26 amino acid residues, most preferably an amino acid sequence consisting of 13 to 20 amino acid residues.

In the present invention, the "amino acid" is used in the broadest sense and includes not only a protein-constituting amino acid but a non-protein-constituting amino acid such as an amino acid variant and derivative. Those skilled in the art should understand in consideration of this broad definition that examples of the amino acid according to the present invention include: protein-constituting L-amino acids; D-amino acids; chemically modified amino acids such as amino acid variants and derivatives; non-protein-constituting amino acids such as norleucine, β-alanine, and ornithine; and chemically synthesized compounds having properties known in the art as features of the amino acid. Examples of the non-protein-constituting amino acid include α-methyl-amino acids (α-methylalanine, etc.), D-amino acids, histidine-like amino acids (2-amino-histidine, β-hydroxy-histidine, homohistidine, α-fluoromethyl-histidine and α-methyl-histidine, etc.), amino acids having extra methylene in a side chain ("homo" amino acids) and amino acids with a carboxylic acid functional group amino acid, in a side chain, substituted by a sulfonic acid group (cysteic acid, etc.). In a preferred aspect of the present invention, the amino acid used in the present invention can be a protein-constituting amino acid.

In the present invention, the polar amino acid residues are not particularly limited as long as the polar amino acid residues are amino acid residues whose side chain can have polarity. The polar amino acid residues include, for example, acidic amino acid residues and basic amino acid residues. In the present specification, the acidic amino acid residues include, for example, an aspartic acid (Asp: D) residue and glutamic acid (Glu: E). The basic amino acids include, for example, arginine (Arg: R), lysine (Lys: K), and histidine (His: H).

In the present specification, for example, the term "aspartic acid (Asp: D)" means that a three-letter code "Asp" and a one-letter code "D" may be used as the abbreviations of the aspartic acid.

In the present specification, among neutral amino acid residues, amino acid residues containing a hydroxy group, an acid amide group, a thiol group, or the like are included in the polar amino acid residues because of having polarity. In the present specification, for example, tyrosine (Tyr: Y), serine (Ser: S), threonine (Thr: T), asparagine (Asn: N), glutamine (Gln: Q), and cysteine (Cys: C) are included in the polar amino acid residues.

In the present specification, the nonpolar amino acid residues are not particularly limited as long as the nonpolar amino acid residues are amino acids whose side chain has no polarity. The nonpolar amino acid residues include, for example, alanine (Ala: A), valine (Val: V), leucine (Leu: L), isoleucine (Ile: I), methionine (Met: M), phenylalanine (Phe: F), tryptophan (Trp: W), glycine (Gly: G), and proline (Pro: P).

When the self-assembling peptide used in the present invention comprises an "amino acid sequence in which polar amino acid residues and nonpolar amino acid residues are alternately arranged", this peptide can have a repeat sequence of "RADA" (2 to 8 repeats, preferably 3 to 6 repeats) or a repeat sequence of "IEIK" (1 to 4 repeats, preferably 2 to 3 repeats) and can be more preferably a peptide comprising RADARADARADARADA (SEQ ID NO: 1) or a peptide comprising IEIKIEIKIEIKI (SEQ ID NO: 2). Further preferably, the self-assembling peptide used in the present invention can be a peptide consisting of RADARADARADARADA (SEQ ID NO: 1) or a peptide consisting of IEIKIEIKIEIKI (SEQ ID NO: 2).

When the self-assembling peptide used in the present invention is a "peptide comprising an amino acid sequence consisting of 13 amino acid residues, wherein nonpolar amino acids and polar amino acids are arranged alternately and at symmetric positions in directions toward the N terminus and the C terminus centered on a nonpolar amino acid residue at position 7", preferably, the "nonpolar amino acid residue at position 7" of this peptide can be alanine (Ala: A). More preferably, the peptide can be a peptide comprising RLDLRLALRLDLR (SEQ ID NO: 3), further preferably, a peptide consisting of RLDLRLALRLDLR (SEQ ID NO: 3).

Other examples of the self-assembling peptide which can be used in the present invention can include peptides disclosed in WO2006/014570.

The self-assembling peptide used in the present invention may be modified (or labeled) as long as the peptide does not lose the main properties intended by the present invention. Such a modified (or labeled) peptide is also included in the "self-assembling peptide" according to the present invention. A method for modifying (or labeling) the self-assembling peptide used in the present invention can be arbitrarily selected by those skilled in the art. For example, the attachment of a functional group or the like, the attachment of a chemical substance, or the attachment of an additional protein or peptide can be performed. Examples of the attachment of a functional group or the like can include acylation, acetylation, alkylation, amidation, biotinylation, formylation, carboxylation, glutamylation, glycosylation (attachment of a sugar chain), glycylation, hydroxylation, isoprenylation, lipoylation, the attachment of a nucleotide or its derivative, polyethylene glycolation (PEGylation), and the attachment of a lipid chain. Examples of the attachment of a chemical substance can include the attachment of an appropriate labeling agent, for example, radioisotopes (e.g., $^{125}I$, $^{131}I$, $^{3}H$, and $^{14}C$), enzymes (e.g., β-galactosidase, β-glycosidase, alkaline phosphatase, peroxidase, and malate dehydrogenase), fluorescent materials (e.g., fluorescamine and fluorescein isothiocyanate), luminescent materials (e.g., luminol, luminol derivatives, luciferin, and lucigenin), and affinity tags (e.g., biotin). Examples of the attachment of an additional protein or peptide can include ISGylation, SUMOylation, and ubiquitination.

The concentration of the self-assembling peptide in the composition of the present invention can be at least approximately 0.5% by weight, at least approximately 1% by weight, at least approximately 1.5% by weight, at least approximately 2% by weight, at least approximately 2.5% by weight, at least approximately 3% by weight, at least approximately 3.5% by weight, at least approximately 4% by weight, at least approximately 4.5% by weight, at least approximately 5% by weight, at least approximately 5.5% by weight, at least approximately 6% by weight, at least approximately 6.5% by weight, at least approximately 7% by weight, at least approximately 7.5% by weight, or at least approximately 8% by weight. Preferably, the concentration of the self-assembling peptide in the composition of the present invention can be at least approximately 1.5% by weight.

The composition of the present invention may further contain one or more biologically active substances (e.g., substances useful in hemostasis and substances useful in the promotion of wound healing) without substantially influencing the ability of the self-assembling peptide to self-assemble in the composition. Examples of such substances include synthetic or natural organic molecules, nucleic acid molecules, various cytokines, and various chemokines. A growth factor may also be contained alone or in combination with a different biologically active substance in the composition of the present invention. Examples of the growth factor include, but are not limited to, epidermal growth factors, nerve growth factors, transforming growth factors alpha and beta, platelet-derived growth factors, insulin-like growth factors, vascular endothelial growth factors, hematopoietic cell growth factors, heparin binding growth factors, acidic fibroblast growth factors, basic fibroblast growth factors, hepatocyte growth factors, brain-derived neurotrophic factors, keratinocyte growth factors, bone morphogenic proteins, and cartilage-derived growth factors.

The terms used in the present specification are given for illustrating particular embodiments and are not intended to limit the invention.

The term "comprising" used in the present specification means that described items (members, steps, factors, numbers, etc.) are present and the presence of the other items (members, steps, factors, numbers, etc.) is not excluded therefrom, unless the context evidently requires different interpretation.

All the terms (including technical terms and scientific terms) used herein have the same meanings as those understood in a broad sense by those skilled in the art to which the present invention belongs, unless otherwise defined. The terms used herein should be interpreted as having meanings consistent with those in the present specification and related technical fields, unless otherwise defined, and should not be interpreted in an idealized or excessively formal sense.

Terms such as "first" or "second" may be used for expressing various factors. However, it is understood that these factors should not be limited by these terms. These terms are used merely for differentiating one factor from the other factors. For example, the first factor may be described as the second factor, and vice versa, without departing from the scope of the present invention.

Hereinafter, the present invention will be described more specifically with reference to Examples. However, the present invention can be embodied in various forms and must not be interpreted as being limited to Examples described herein.

EXAMPLES

<Object of Test>

Oozing bleeding was created by abrading the porcine liver using a metal file. A self-organizing peptide solution was applied to the bleeding by usual application or spray application and evaluated for its hemostatic effect and applied amount.

<Guideline of Test Practice>

This test was conducted as a non-GLP test.

<Animal Protection>

This test was conducted with the approval of the Institutional Animal Care and Use Committee according to "rules and regulations for the contact of animal experiments" provided by NAS Laboratory Co., Ltd. as to the items of animal experiments to be practiced from a scientific standpoint and under ethical consideration, on the basis of "Act on Welfare and Management of Animals (Act No. 105 of 1973)", "Standards Relating to the Care and Management of Laboratory Animals and Relief of Pain (Notice. No. 88 of the Ministry of the Environment, 2006)", "Basic Policies for Conduct of Animal Experiments" of the Ministry of Agriculture, Forestry and Fisheries and the Ministry of Health, Labour and Welfare, and "Guidelines for Proper Conduct of Animal Experiments (Science Council of Japan, Jun. 1, 2006)".

<Test Animal>

Animal species: pig

Breed: LWD

Sex: female

The number of animals introduced: 2

Age in days at the time of introduction: any

Body weight at the time of introduction: 50 kg Institute receiving the animals: Narita experimental laboratory of NAS Laboratory Co., Ltd.

Distributor of the animals: Ishige Tikusan

Acclimatization period: approximately 7 days after introduction

Quarantine: the absence of abnormalities was confirmed by quarantine under clinical observation at the time of introduction and during the acclimatization period.
Individual discrimination: ear tag
<Rearing Conditions>
(1) Rearing Environment The test animals were each individually raised in a stainless cage (W: 690×D: 960×H: 740 mm) of a rearing room with a temperature and a humidity set. The temperature and the humidity were controlled using an air conditioner set to 25±3° C. and 60±10%, respectively. Illumination was set to 12-hour light and 12-hour dark periods (light period: 7:00 to 19:00). The cleaning of the cage and a feeder and the cleaning and disinfection of the rearing room were carried out every day.

(2) Type of Feed, Amount of Feed and Feeding Method

The feed used was "Breed 74" (JA Higashinihon Kumiai Shiryo Co., Ltd.) and was given to the animals twice a day (AM and PM) in an amount of 250 g per meal. However, on the day of the experiment, the animals were not fed in order to avoid misswallowing due to vomiting when anesthetized, etc.

(3) Drinking of Water

For feeding of water, the animals were allowed to freely drink well water using an automatic feed-water apparatus. Substance concentrations and bacterial counts in the drinking water were analyzed once a year, and the analysis values were confirmed to conform to the water quality criteria of the Water Supply Act.

<Individual Discrimination and Constitution of Test Group>

The individual discrimination of the animals was performed using ear tag numbers. The entrances of the rearing rooms were marked with test numbers and test periods, and the cages indicated test numbers, test groups, and animal numbers.

<Pretreatment and Anesthetic Administration Method>

Atropine sulfate was intramuscularly administered at 0.05 mg/kg (dosing volume: 0.1 mL/kg) to each animal. Approximately 30 minutes later, 20 mg/kg (dosing volume: 0.4 mL/kg) of ketamine hydrochloride and 4 mg/kg (dosing volume: 0.2 mL/kg) of xylazine hydrochloride were mixed and intramuscularly administered thereto. Each anesthetic was introduced by the intramuscular administration to the ear root using a disposable syringe (Terumo Corp.) attached with an 18 G injection needle (Terumo Corp.). Then, a tracheal tube (TOP intratracheal tube, TOP Corp.) was intubated, and the anesthesia was maintained with isoflurane using an inhalation anesthesia apparatus SUBARU-KJ02 (Mikasa Kantou Syoukai Co., Ltd.) and a mechanical ventilator (COMPOS β-EV, Metran Co., Ltd.). The perioperative isoflurane concentration was set to 1 to 3%, and the amount of oxygen was set to 2 L/min. The intrapulmonary pressure of the mechanical ventilator was set to 15 cmH2O, and the respiratory rate was set to 15 times/min. Each animal was placed supine on an operating table and covered with a sterilized drape.

<Perioperative Monitoring>

An electrocardiogram, a pulse oximeter, and a thermometer were set up, and perioperative monitoring was carried out. Blood pressure was bloodlessly measured by setting up a cuff for blood pressure measurement. The blood pressure was maintained at an average blood pressure of 60 mmHg or higher.

<Test Substance>

The peptide solutions (test substances) used in this experiment and their storage elastic moduli are shown in the table below.

TABLE 1

| | Before application | |
|---|---|---|
| | Storage elastic modulus G' (Pa) (mean: N = 3) | SD |
| Peptide No. 1 1.0% (pH no treatment) | 30 | 3.9 |
| Peptide No. 1 1.5% (pH no treatment) | 75 | 9.5 |
| Peptide No. 1 2.0% (pH no treatment) | 141 | 8.1 |
| Peptide No. 1 2.5% (pH no treatment) | 503 | 22.4 |
| Peptide No. 2 1.0% (pH 3.0) | 349.0 | 45.5 |
| Peptide No. 2 1.5% (pH 3.0) | 2,309 | 50.5 |
| Peptide No. 3 1.0% (pH 7.5) | 75 | 5.4 |
| Peptide No. 3 1.5% (pH 7.5) | 239 | 19.9 |
| Peptide No. 3 2.0% (pH 7.5) | 439 | 12.1 |

(Peptide concentration: % by weight)

```
                                       (SEQ ID NO: 1)
        Peptide No. 1: RADARADARADARADA (SEQ ID NO: 2)
        Peptide No. 2: IEIKIEIKIEIKI (SEQ ID NO: 3)
        Peptide No. 3: RLDLRLALRLDLR
```

For All the peptides described above, the bulk powder was synthesized by CPC Scientific, Inc. All the peptides were N-terminally acetylated and C-terminally amidated. Purified water of Japanese Pharmacopoeia was used as a solvent for the peptides.

Frequency sweep tests were conducted from 1 rad/sec to 10 rad/sec at a shear stress of 1 Pa, and the storage elastic modulus at 10 rad/sec was selected as data. As for a viscosity before gelling, tests were conducted for a soaking time of 2 min by loading each peptide solution between 20 mm plates with a gap distance of 500 um.

<Testing Method>

1. Each completely anesthetized pig was laparotomized by abdominal midline incision using a surgical knife and an electric surgical knife to expose the liver.

2. Oozing bleeding was created by abrading the liver using a metal file.

3. Each test substance was applied to the bleeding inclined plane by usual application (*1) or spray application (*2).

4. The time from after the end of application to the end of assessment of the completion of hemostasis was measured using a stopwatch (*3). The amount of each test substance used until the end of the test was recorded.

*1: A syringe was packed with the peptide solution (test substance), and the peptide solution was pushed out of a nozzle at the tip of the syringe and thereby applied to the subject (see the syringe of FIG. 1).

*2: A syringe (equivalent to that of FIG. 1) packed with the peptide solution (test substance) was loaded in a spray gun, and compressed air was blown to a nozzle at the tip of the syringe using a compressor so that the peptide solution pushed out of the nozzle was sprayed to the subject. The spray pressure was generally 0.5 to 1.5 [kgf/cm2], though differing depending on the viscosity of each test substance, the status of bleeding, and the distance to the application site.

*3: If bleeding was not weakened after initial application (if it was judged that this condition would not lead to hemostasis), additional application was appropriately performed. The time of completion of initial application was defined as the start of measurement, and the time of completion of hemostasis assessment was defined as the end of measurement.

RESULTS

In the tests described above, the way in which each peptide solution was applied to the bleeding site of the liver is shown in FIGS. 2 to 5. As seen in the drawings, the peptide solution was nonuniformly spread over the bleeding site by the usual administration, whereas the peptide solution was uniformly spread over the bleeding site by the spray application.

Figures 6, 7:
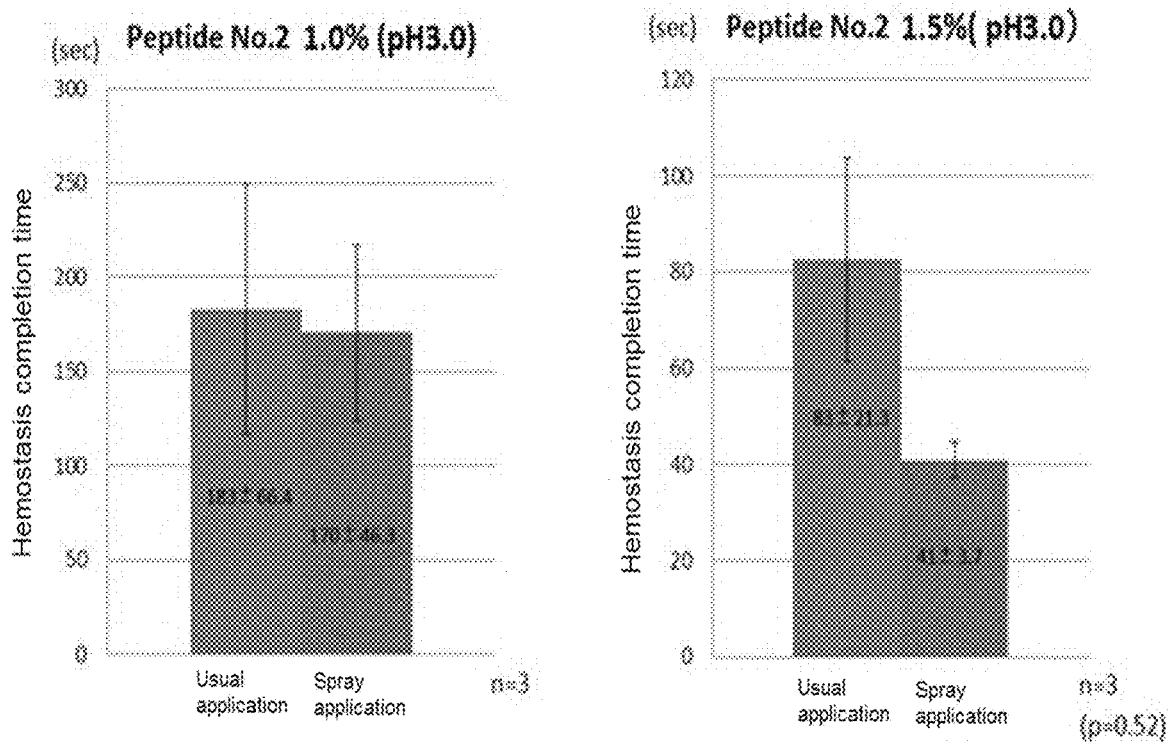
FIG. 6 shows results of measuring a hemostasis completion time and the amount of a composition applied until the completion of hemostasis, when Peptide No. 1 (1.0%, 1.5%, 2.0%, or 2.5%) was applied to a bleeding site of the porcine liver by usual application or spray application.
FIG. 7 shows results of measuring a hemostasis completion time Peptide No. 2 (1.0% or 1.5%) was applied to a bleeding site of the porcine liver by usual application or spray application.

As shown in FIG. 6, the peptide solution containing Peptide No. 1 at the concentration of 1.0% had tendencies of a shorter hemostasis completion time and a smaller amount of the solution applied until hemostasis, in the spray application group than in the usual application group, though there was no significant difference. On the other hand, the concentrations of 1.5% or higher evidently resulted in a shorter hemostasis completion time and a smaller amount of the solution applied until hemostasis, in the spray application group than in the usual application group.

Figures 8, 9:
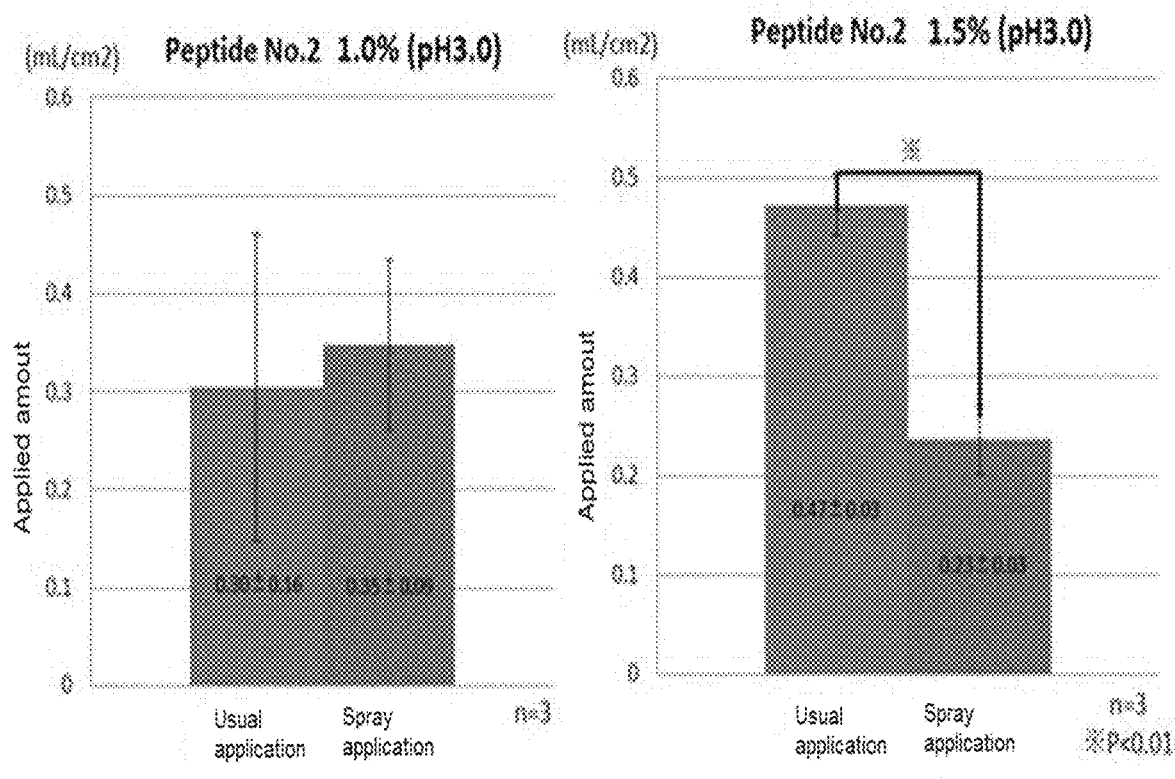
FIG. 8 shows results of measuring the amount of a composition applied until the completion of hemostasis when Peptide No. 2 (1.0% or 1.5%) was applied to a bleeding site of the porcine liver by usual application or spray application.
FIG. 9 shows results of measuring a hemostasis completion time and the amount of a composition applied until the completion of hemostasis, when Peptide No. 3 (1.5%) was applied to a bleeding site of the porcine liver by usual application or spray application.

As shown in FIGS. 7 and 8, the peptide solution containing Peptide No. 2 at the concentration of 1.0% also exhibited no significant difference in results between the spray application group and the usual application group, as in the results about the peptide solution containing Peptide No. 1. By contrast, the concentration of 1.5% evidently resulted in a shorter hemostasis completion time and a smaller amount of the solution applied until hemostasis, in the spray application group than in the usual application group.

As shown in FIG. 9, the peptide solution containing Peptide No. 3 also succeeded in hemostasis in the spray application group, but failed in hemostasis by the usual application.

These results demonstrated that, surprisingly, a solution containing the self-assembling peptide, when used as a spray, exerts an improved hemostatic ability as compared with that when usually administered.

The invention claimed is:

1. A method for hemostasis in a subject, comprising the step of
applying a composition comprising a self-assembling peptide to a bleeding site of the subject by spraying the composition on the bleeding site at a pressure of 0.5 to 1.5 kgf/cm2, wherein
the self-assembling peptide self-assembles and thereby gels when the composition is applied to the bleeding site of the subject,
the self-assembling peptide is a peptide comprising IEIKIEIKIEIKI (SEQ ID NO: 2), and
the concentration of the self-assembling peptide in the composition is 1.5% to 3% by weight.

2. The method according to claim 1, wherein
the bleeding site of the subject is a non-surgically formed wound site or a surgically formed incision site or excision site.

3. The method according to claim 1, wherein
the subject is a nonhuman animal.

* * * * *